(12) United States Patent
Rohling et al.

(10) Patent No.: US 10,512,508 B2
(45) Date of Patent: Dec. 24, 2019

(54) IMAGERY SYSTEM

(71) Applicant: The University of British Columbia, Vancouver (CA)

(72) Inventors: Robert Rohling, Vancouver (CA); Philip Edgcumbe, Vancouver (CA); Christopher Nguan, Vancouver (CA)

(73) Assignee: The University of British Columbia (CA)

( * ) Notice: Subject to any disclaimer, the term of this patent is extended or adjusted under 35 U.S.C. 154(b) by 295 days.

(21) Appl. No.: 15/183,458

(22) Filed: Jun. 15, 2016

(65) Prior Publication Data

US 2016/0360954 A1    Dec. 15, 2016

Related U.S. Application Data

(60) Provisional application No. 62/175,595, filed on Jun. 15, 2015.

(51) Int. Cl.
*H04N 13/20* (2018.01)
*A61B 34/20* (2016.01)
(Continued)

(52) U.S. Cl.
CPC .......... *A61B 34/20* (2016.02); *H04N 5/2256* (2013.01); *H04N 13/254* (2018.05); *A61B 1/313* (2013.01);
(Continued)

(58) Field of Classification Search
CPC .. H04N 13/0239; A61B 17/0206; A61B 34/20
(Continued)

(56) References Cited

U.S. PATENT DOCUMENTS 6,503,195 B1   1/2003   Keller et al.
6,549,288 B1   4/2003   Migdal et al.
(Continued)

FOREIGN PATENT DOCUMENTS

CN   101762243 A   6/2010
CN   101836852 A   9/2010
(Continued)

OTHER PUBLICATIONS

Fuchs et al.; "Augmented Reality Visualization for Laparoscopic Surgery"; In MICCAI 1998, LNCS, vol. 1496. pp. 934-943.
(Continued)

*Primary Examiner* — Jefferey F Harold
*Assistant Examiner* — Sihar A Karwan
(74) *Attorney, Agent, or Firm* — BakerHostetler

(57) ABSTRACT

An imagery system includes: a camera having a field of view; a light source including a source of structured light, the light source movable relative to the camera; and at least one processor. The at least one processor is programmed to determine, at least, estimated locations of points on a surface exposed to the structured light according to image data received from the field of view of the camera. The light source may include at least one fiducial marker, and the at least one processor may be programmed to determine the estimated position of the source of structured light according to the at least one fiducial marker in the image data. Also, the camera may be a stereoscopic camera.

22 Claims, 11 Drawing Sheets

(51) Int. Cl.
| | |
|---|---|
| H04N 5/225 | (2006.01) |
| H04N 13/254 | (2018.01) |
| A61B 1/313 | (2006.01) |
| H04N 13/00 | (2018.01) |
| A61B 17/34 | (2006.01) |

(52) U.S. Cl.
CPC ... *A61B 17/3415* (2013.01); *A61B 2034/2057* (2016.02); *H04N 2005/2255* (2013.01); *H04N 2013/0081* (2013.01)

(58) Field of Classification Search
USPC .......................................... 348/44; 600/202
See application file for complete search history.

(56) References Cited

U.S. PATENT DOCUMENTS

| | | | |
|---|---|---|---|
| 6,764,185 | B1 | 7/2004 | Beardsley et al. |
| 7,728,868 | B2 | 6/2010 | Razzaque et al. |
| 8,482,606 | B2 | 7/2013 | Razzaque et al. |
| 8,504,136 | B1 | 8/2013 | Sun et al. |
| 9,155,520 | B2 | 10/2015 | Schneider et al. |
| 9,621,861 | B2 * | 4/2017 | Hiranuma ............ H04N 9/3185 |
| 2004/0073278 | A1 | 4/2004 | Pachys |
| 2010/0060718 | A1 | 3/2010 | Forster |
| 2012/0310098 | A1 | 12/2012 | Popovic |
| 2013/0027515 | A1 * | 1/2013 | Vinther .............. A61B 1/00177 348/44 |
| 2013/0218024 | A1 | 8/2013 | Boctor |
| 2013/0237811 | A1 * | 9/2013 | Mihailescu ............ A61B 5/064 600/424 |
| 2013/0278725 | A1 | 10/2013 | Mannan |
| 2015/0018622 | A1 * | 1/2015 | Tesar ...................... A61B 1/05 600/202 |

FOREIGN PATENT DOCUMENTS

| | | |
|---|---|---|
| CN | 202631778 U | 12/2012 |
| WO | WO 2003/105289 A2 | 12/2003 |
| WO | WO 2008/052348 A1 | 5/2008 |
| WO | WO 2010/021972 A1 | 2/2010 |
| WO | WO 2012/047410 A1 | 4/2012 |
| WO | WO 2012/142064 A2 | 10/2012 |
| WO | WO 2013/163391 A1 | 10/2013 |

OTHER PUBLICATIONS

Maier-Hein et al.; "Optical Techniques for 3D Surface Reconstruction in Computer-Assisted Laparoscopic Surgery"; Medical Image Analysis; vol. 17; 2013; p. 974-996.
Clancy et al.; "Spectrally Encoded Fiber-Based Structured Lighting Probe for Intraoperative 3D Imaging"; Biomedical Optics Express; vol. 2 No. 11; Nov. 2011; p. 3119-3128.
Lincoln; March of the Pico Projectors; IEEE Spectrum. 47; Apr. 2010; 7 pages.
Park et al.; "Surface-Independent Direct-Projected Augmented Reality"; ACCV 2006 LNCS, vol. 3852; 2006 pp. 892-901.
Tardif et al.; "Projector-based augmented reality in surgery without calibration"; Int'l Conf. of the IEEE EMBS; Sep. 2003; pp. 548-551.
Edgcumbe et al.; "Calibration and Stereo Tracking of a Laparoscopic Ultrasound Transducer for Augmented Reality in Surgery"; AR Environments for Med. Imag. and Computer-Assisted Interventions,; vol. 8090; 2013; pp. 258-267.
Geng; "Structured-Light 3D Surface Imaging: a Tutorial"; Advances in Optics and Photonics 3; 2011; p. 128-160.
Falcao et al.; "Plane-based calibration of a projector-camera system."; VIBOT Master 2008; 12 pages.
Hughes-Hallett et al.; "Intraoperative Ultrasound Overlay in Robot-assisted Partial Nephrectomy: First Clinical Experience"; European Urology; vol. 65; 2014 p. 671-672.
Lin et al.; "Dense Surface Reconstruction with Shadows in MIS"; IEEE Transactions on Biomedical Engineering; vol. 60 No. 9; Sep. 2013; p. 2411-2420.
Sun; "Image guided interaction in minimally invasive surgery"; (M.A.Sc. Thesis) Simon Fraser University (http://summit.sfu.ca/item/12097) Burnaby, Canada 80-84; 2012; 140 pages.
Gavaghan et al; "A portable image overlay projection device for computer-aided open liver surgery"; IEEE Transactions on Biomedical Engineering; vol. 58 No. 6; Jun. 2011; p. 1855-1864.
Gavaghan et al.; "Evaluation of a portable image overlay projector for the visualisation of surgical navigation data: phantom studies;"; International journal of computer assisted radiology and surgery 7.4; 2012; p. 547-556.
Hansen et al.; "Illustrative visualization of 3D planning models for augmented reality in liver surgery"; International journal of computer assisted radiology and surgery 5; No. 2; 2010; p. 133-141.
Hayashibe et al.; "Laser-scan endoscope system for intraoperative geometry acquisition and surgical robot safety management;" Medical Image Analysis 10, No. 4; 2006; p. 509-519.
Maurice et al.; "A structured light-based laparoscope with real-time organs' surface reconstruction for minimally invasive surgery."; $34^{th}$ Annual Int'l Conf. of the IEEE EMBS; Sep. 2012; pp. 5769-5772.
Reiter et al.; "Surgical structured light for 3d minimally invasive surgical imaging" In 2014 IEEE/RSJ International Conference on Intelligent Robots and Systems; 2014; pp. 1282-1287.
Schneider et al.; "Intra-operative "Pick-Up" Ultrasound for Robot Assisted Surgery with Vessel Extraction and Registration: A Feasibility Study"; IPCAI 2011, LNCS; vol. 6689, 2011; pp. 122-132.
Bouguet; "Visual Methods for Three-dimensional Modeling;" PhD Thesis, 30-124; 1999; 236 pages.
Zhang; "Flexible New Technique for Camera Calibration"; IEEE Transactions on Pattern Analysis and Machine Intelligence; vol. 22; 2000; 22 pages.
Pratt et al.; "Intraoperative ultrasound guidance for transanal endoscopic microsurgery" MICCAI; vol. 7510; 2012; pp. 463-470.
Salvi et al.; "Pattern Codification Strategies in Structured Light Systems"; Pattern Recognition vol. 37(4); Apr. 2014; 26 pages.
Ma et al.; "Binocular structured light stereo matching approach for dense facial disparity map"; Advances in Artificial Intelligence; 2011; pp. 550-559.
Hirschmuller; "Stereo processing by semiglobal matching and mutual information", IEEE Transactions on Pattern Analysis and Machine Intelligence; vol. 30, No. 2; Feb. 2008; pp. 328-341.
Edgcumbe et al.; "Pico Lantern: Surface reconstruction and augmented reality in laparoscopic surgery using a pick-up laser projector"; Medical Image Analysis, vol. 25; 2015; p. 95-102.
Edgcumbe et al.; "Pico Lantern: a pick-up projector for augmented reality in laparoscopic surgery"; Medical Image Comput. Comput. Assist Interv., 17(Pt 1); 2014; p. 432-439.
Schmalz et al.; "An endoscopic 3D scanner based on structured light"; Medical Image Analysis; vol. 16; 2012; p. 1063-1072.
https://code.google.com/archive/p/procamcalib/; Projector-Camera Calibration Toolbox; Google; accessed Sep. 15, 2016; 2 pages.

* cited by examiner

IMAGERY SYSTEM

CROSS-REFERENCE TO RELATED APPLICATION

This application claims the benefit of, and priority to, U.S. provisional patent application No. 62/175,595 filed on Jun. 15, 2015, the entire contents of which are incorporated by reference herein.

FIELD

This disclosure relates generally to imagery, for example in minimally invasive surgery or in other applications.

RELATED ART

Minimally invasive surgery can involve operating surgical tools in a body cavity that is accessible through one or more small incisions, and that may be inflated to facilitate operating the surgical tools in the body cavity. For example, tools for minimally invasive surgery can include a da Vinci™ robotic system (available from Intuitive Surgical, Inc. of Sunnyvale, Calif., United States of America), and can include a camera such as an endoscope (to examine organs including the throat or esophagus), a laparoscope (to examine the abdomen or pelvis internally), an arthroscope (to examine joints), a cystoscope (to examine the bladder), a nephroscope (to examine the kidneys), a bronchoscope (to examine bronchi), or a colonoscope (to examine the colon), for example.

Often, minimally invasive surgery requires accurate and precise guidance in view of sub-surface anatomy such as tumors, blood vessels, and nerves. However, minimally invasive surgery with a camera only depicts surface anatomy. Moreover, minimally invasive surgery is typically limited to small spaces, and some imaging systems for minimally invasive surgery can provide limited information to visualize such small spaces. For example, depth perception and measurement during minimally invasive surgery can be limited in some imaging systems. Further, surgery often operates on smooth featureless organ tissue, which can be difficult to perceive using some imaging systems.

SUMMARY

According to one embodiment, there is provided an imagery system comprising: a camera having a field of view; and a light source comprising a source of structured light and at least one fiducial marker visible externally from the light source, the light source movable relative to the camera. The system further comprises at least one processor programmed to determine, at least: an estimated position of the source of structured light according to representations of the at least one fiducial marker in image data received from the field of view of the camera; and estimated locations, in a three-dimensional co-ordinate system, of points on a surface exposed to the structured light according to the image data and according to the estimated position of the source of structured light.

In some embodiments, the at least one fiducial marker comprises at least one two-dimensional label on the light source.

In some embodiments, the at least one processor is further programmed to cause the light source to project surgical guidance information according to the estimated position of the source of structured light.

In some embodiments, the at least one processor is further programmed to: identify at least one location on the surface having surface movements; and cause the light source to project light indicating the surface movements on the at least one location on the surface having the surface movements.

In some embodiments, the light source comprises a tool interface configured to be held by a laparoscopic tool in a unique stable position relative to the laparoscopic tool.

In some embodiments, the at least one processor is further programmed to generate a representation of the points on the surface from a point of view different from a point of view of the camera. In some embodiments, the light source is independently movable relative to the camera.

In some embodiments, the light source is sized to fit through a cannula of a laparoscopic trocar.

In some embodiments, the light source is sized to fit through an orifice having a diameter less than 15 millimeters.

In some embodiments, the estimated position of the source of structured light comprises an estimated linear position and an estimated angular position of the source of structured light.

In some embodiments, the camera is a laparoscopic camera. In some embodiments, the camera is a smartphone camera.

In some embodiments, the at least one processor is programmed to determine the estimated locations of the points on the surface at a rate of at least ten times per second.

In some embodiments, the light source is a source of multi-color light.

In some embodiments, the light source is sterilizable.

In some embodiments, the light source comprises one or more laser diodes and a mirror movable relative to the one or more laser diodes and positioned to direct light from the one or more laser diodes.

According to one embodiment, there is provided an imagery system comprising: a stereoscopic camera having a field of view; a light source comprising a source of structured light, the light source movable relative to the stereoscopic camera and comprising a tool interface configured to be held by a laparoscopic tool in a unique stable position relative to the laparoscopic tool; and at least one processor programmed to determine, at least, estimated locations, in a three-dimensional co-ordinate system, of points on a surface exposed to the structured light according to image data of the surface received from the field of view of the stereoscopic camera.

In some embodiments, the at least one processor is further programmed to determine an estimated position of the source of structured light according to the image data.

In some embodiments, the at least one processor is further programmed to cause the light source to project surgical guidance information according to the estimated position of the source of structured light.

Other aspects and features will become apparent to those ordinarily skilled in the art upon review of the following description of illustrative embodiments in conjunction with the accompanying figures.

DETAILED DESCRIPTION

Figure 1:
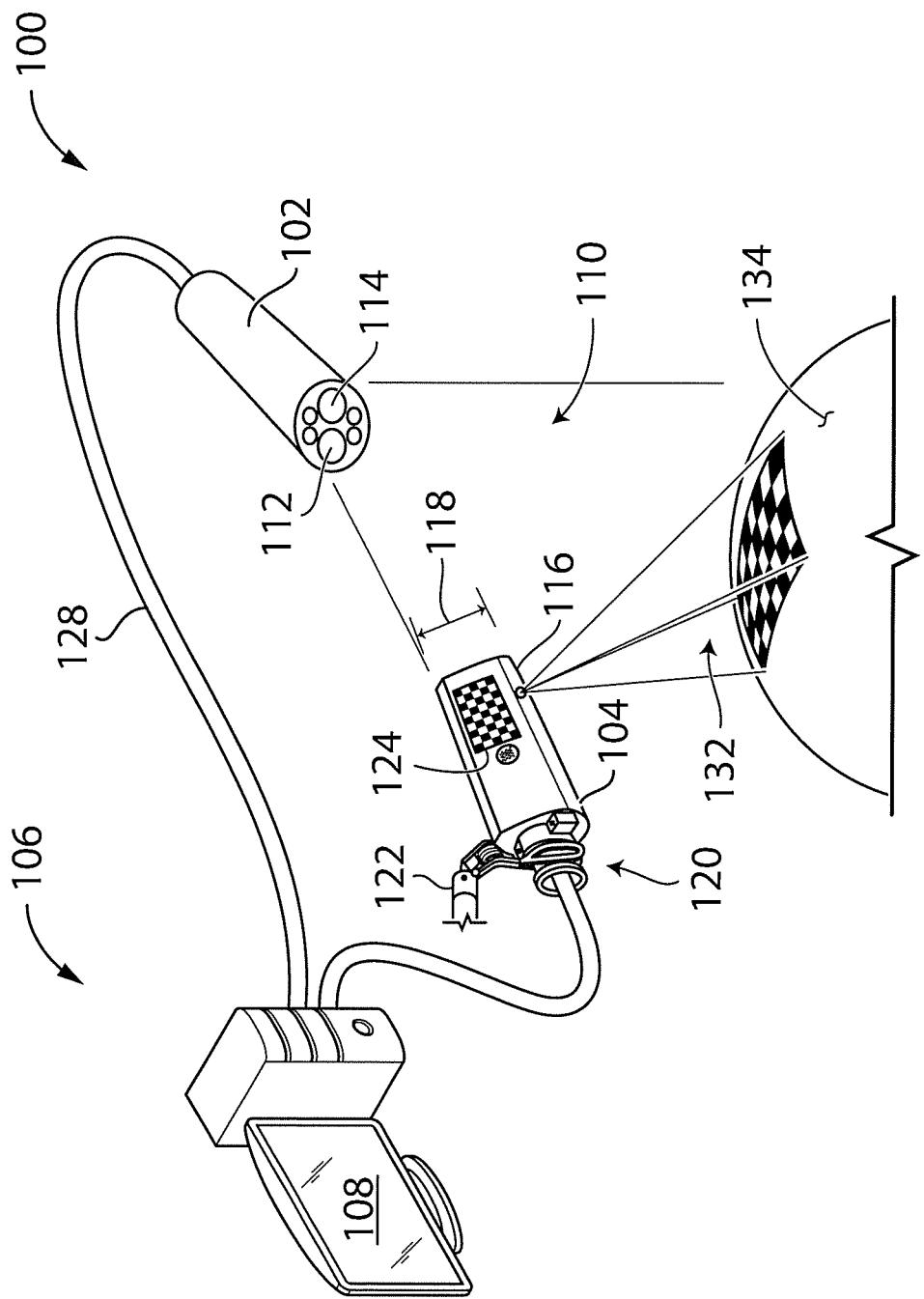
FIG. 1 is a perspective view of an imagery system according to one embodiment.

Referring to FIG. 1, an imagery system according to one embodiment is shown generally at 100 and includes a camera 102, a light source 104, and a computer shown generally at 106 and including a display screen 108. In some embodiments, the display screen 108 may be a display console for a surgeon, or any other display, such as a display specialized for surgery, for example. The light source 104 is independently movable in six degrees of freedom relative to the camera 102.

The camera 102 in the embodiment shown is a laparoscopic camera of a da Vinci™ robotic system and designed for minimally invasive surgery in an abdomen or pelvis, but cameras in alternative embodiments may include other cameras such as endoscope, an arthroscope, a cystoscope, a nephroscope, a bronchoscope, a colonoscope, a smartphone camera, or a tablet-computer camera, for example. The camera 102 has a resolution of 1280×1024 pixels and field of view shown generally at 110. Also, in the embodiment shown, the camera 102 is a stereoscopic camera having two lenses 112 and 114 that are spaced apart from each other in a fixed relation to each other, and that can capture three-dimensional images by triangulation of image data of points in the field of view 110 and received through the lenses 112 and 114. However, cameras in alternative embodiments may be monoscopic, for example. Further, the camera 102 in the embodiment shown is a video camera that captures images at one or more than one different frame rate.

Figure 2:
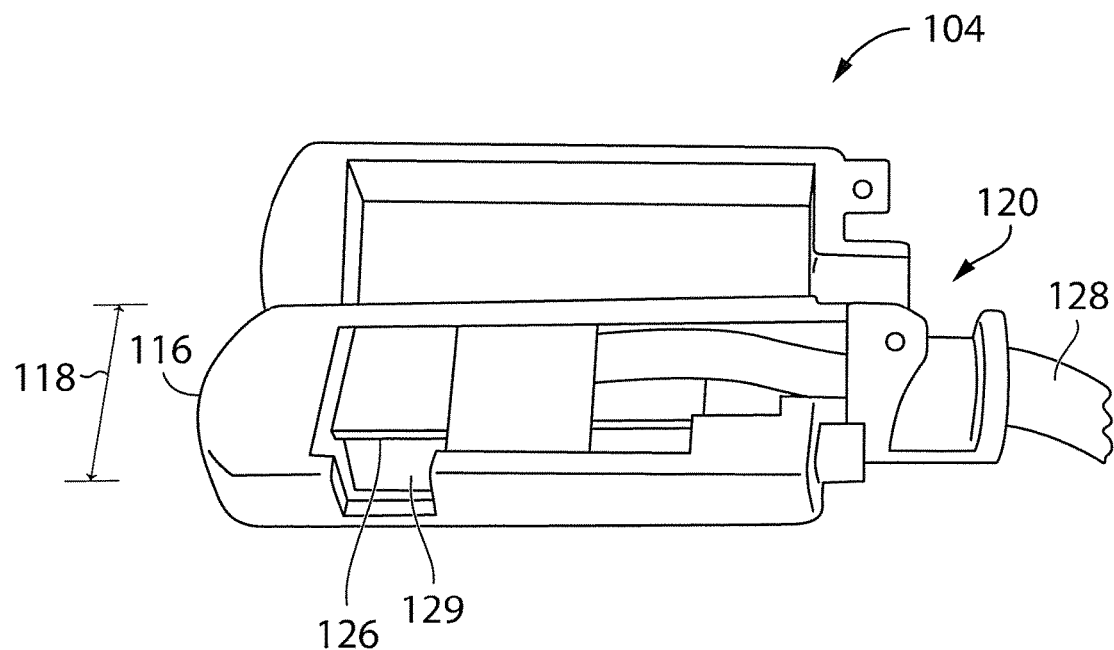
FIG. 2 is a perspective view of a light source of the imagery system of FIG. 1.

The light source 104 in the embodiment shown includes a housing 116, which is shown closed in FIG. 1 and open in FIG. 2. The housing 116 has a diameter or maximum width 118 of 15 millimeters ("mm"), which allows the light source 104 to fit through a cannula of a laparoscopic trocar, which allows the light source 104 to be inserted into an inflated body cavity during laparoscopic surgery. The light source 104 is thus sized to fit through an orifice having a diameter less than 15 mm. However, in other embodiments, the housing 116 may have a diameter or maximum width of 28 mm, which may allow the light source 104 to be inserted through an incision. In other embodiments, the housing 116 may have a diameter or maximum width of less than 30 mm, less than 20 mm, or less than 15 mm, or 12 mm, for example.

In the embodiment shown, the housing 116 includes a grasping element or tool interface shown generally at 120, which is configured to be held by a laparoscopic tool 122 (which may be a robotic laparoscopic tool) in a unique and stable position relative to the laparoscopic tool 122. Such grasping elements and tool interfaces are discussed further in U.S. Pat. No. 9,155,520 and in Schneider, C., Guerrero, J., Nguan, C., Rohling, R., Salcudean, S., Intra-operative "Pick-Up" Ultrasound for Robot Assisted Surgery with Vessel Extraction and Registration: A Feasibility Study, in Taylor, R. H., Yang, G.-Z. (eds.) IPCAI 2011, LNCS, vol. 6689, pp. 122-132, Springer, Heidelberg (2011).

The light source 104 also includes a fiducial marker 124, which in the embodiment shown is a two-dimensional label made from surgical identification tape (available from Key Surgical, Inc. of Minnesota, United States of America) semi-permanently attached to an exterior surface of the housing 116, visible externally from the light source 104, and bearing a checkerboard pattern with 3.175 mm squares. Alternative embodiments may include one, two, or more than two such labels. Further, alternative embodiments may include different fiducial markers, such as matrix barcodes, asymmetric dot patterns, light-emitting diodes, reflective markers, or one or more markers for an electromagnetic tracker, for example. The housing 116 and the fiducial marker 124 are sterilizable, so the light source 104 overall may be sterilizable, which may facilitate the light source 104 to be inserted into a body cavity during minimally invasive surgery.

Figure 3:
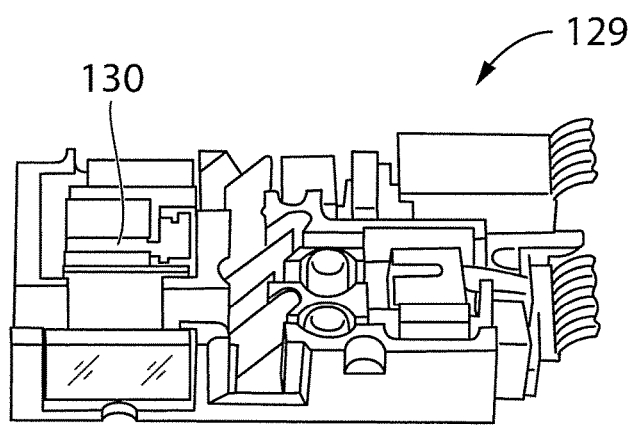
FIG. 3 is a perspective view of a projector of the light source of FIG. 2.

Referring to FIGS. 1 to 3, the light source 104 includes a printed circuit board 126 inside the housing 116 and in communication with the computer 106 through an electronic tether 128. The printed circuit board 126 is in communication with a projector 129. The projector 129 in the embodiment shown is a micro electro mechanical system ("MEMS") projector including one or more laser diodes, a MEMS mirror 130 (2.9×2.2×1 mm in one embodiment) positioned to direct light from the one or more laser diodes, and mechanical and electronic sensors and actuators configured to move the mirror 130 relative to the one or more laser diodes to control a direction of reflected and projected light from the one or more laser diodes. The projector 129 has a high-definition multimedia interface ("HDMI") input, a frame rate of 60 Hertz, a projection resolution of 848×480 pixels, and a brightness of 15 lumens. In general, the projector 129 can project dots, lines, geometric patterns, or arbitrary patterns on a surface.

Light from the projector 129 may be in focus, without requiring any optical lenses, because the projector 129 projects light reflected from one or more laser diodes. When the diameter or maximum width 118 is 12 mm or 15 mm for example, two of the three laser diodes of the MEMS projector may be removed, and the blue laser diode may be moved to a different location. However, in general, light from the projector 129 may be monochromatic, or may be multi-color light such as a combination of red, green, and blue additive colors, for example. Further, light from the projector 129 may have one or more frequencies that are visible to human eyes, one or more frequencies that are invisible to human eyes, or a combination of one or more frequencies that are visible to human eyes and one or more frequencies that are invisible to human eyes. In some embodiments, an integrated photonics module ("IPM") of the MEMS projector may be inside the housing 116, and an electronics platform module ("EPM") of the MEMS projector may be outside of the housing 116 and outside of the patient during surgery. Alternative embodiments may include different projectors or different light sources. For example, in some embodiments, a light source may include a projector outside of the light source housing that may be positioned inside a patient. Rather, in such embodiments, light may be generated in a projector outside of the patient and conveyed through an optical cable and projected inside the patient. In such embodiments, the end of the optical cable that that may be positioned inside the patient may include a fiducial marker as described herein, for example.

The light source 104 is configured to project structured light shown generally at 132 onto a surface 134, so the light source 104 may thus function as source of structured light. The structured light 132 in the embodiment shown is a two-dimensional or planar checkerboard pattern of light having one or more frequencies that are visible to human eyes, but such structured light in alternative embodiments may include other patterns and may include light having one or more frequencies that are invisible to human eyes or a combination of one or more frequencies that are visible to human eyes and one or more frequencies that are invisible to human eyes. Alternative embodiments may include different sources of structured light, such as a uniform light source configured to shine light through a cut-out mask, for example. In various embodiments, the surface 134 may be a surface of human or other animal tissue, such as a surface of a kidney during a partial nephrectomy or a surface of a prostate gland during a radical prostatectomy, for example. Park, H., Lee, M-H. Kim, S-J., Park, J-I., Surface-Independent Direct-Projected Augmented Reality, in Narayanan, P. J., Nayar, S. K., Shum, H.-Y. (eds.), ACCV 2006 LNCS, vol. 3852, pp. 892-901, Springer, Heidelberg (2006) discusses some challenges when projecting on curved non-white surfaces, and Tardif, J.P., Roy, S., Meunier, J., IEEE: Projector-based augmented reality in surgery without calibration, in IEEE EMBS, pp. 548-551, IEEE Press, New York (2003) discusses modification of the structured light in some circumstances. For example, the structured light may include a greater density of points near areas of greater curvature or gradient, and a lesser density of points near areas of lesser curvature or gradient.

Figure 4:
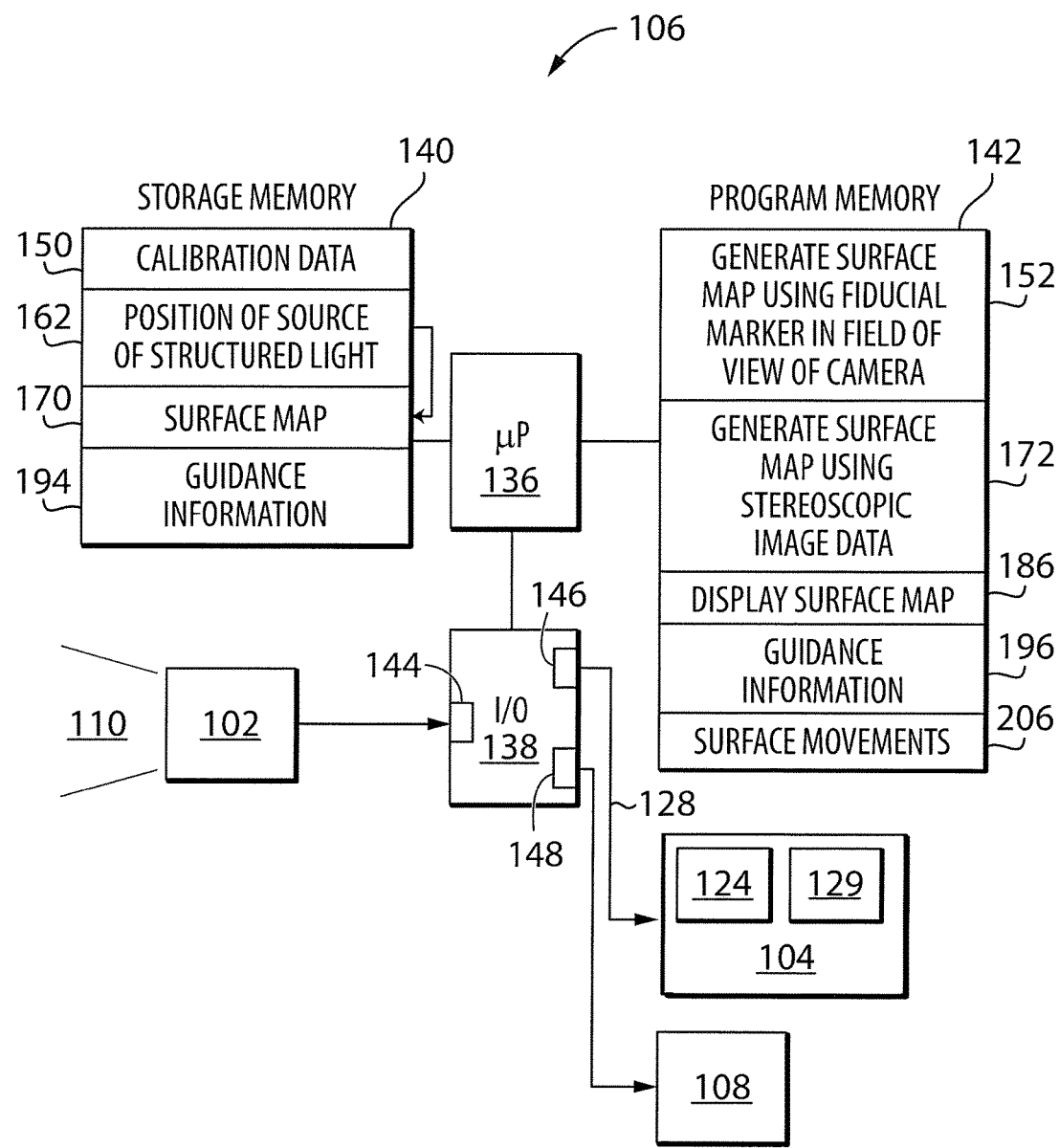
FIG. 4 is a schematic illustration of a computer of the imagery system of FIG. 1.

Referring to FIG. 4, the computer 106 includes a processor circuit, which includes a microprocessor 136 and an input/output ("I/O") interface 138, a storage memory 140, and a program memory 142 all in communication with the microprocessor 136. The I/O interface 138 includes an input signal interface 144 that facilitates receipt of input signals from the camera 102 as described herein for example, an output signal interface 146 that facilitates transmission of output signals through the electronic tether 128 and to the light source 104 to control the light source 104 as described herein for example, and an output signal interface 148 that facilitates transmission of output signals to the display screen 108 to control the display screen 108 as described herein for example.

The storage memory 140 includes various storage blocks for storing data as described below, and the program memory 142 stores executable program codes for directing the microprocessor 136 to execute various functions of the computer 106 as described below. The storage memory 140 and the program memory 142 may be implemented on the same or different ones of, or on a combination of more than one of, a random access memory ("RAM"), a hard disc drive ("HDD"), and other computer-readable or computer-writable memory. In alternative embodiments, the computer 106 may be partially or fully implemented using different hardware logic, which may include discrete logic circuits or an application-specific integrated circuit ("ASIC"), for example.

In some embodiments, the light source 104 may be calibrated and the relative position of the light source 104 and camera 102 determined, as described in Falcao, G., Hurtos, N., Massich, J., Foti, D., Projector-Camera Calibration Toolbox, Erasumus Mundus Masters in Vision and Robotics (2009), for example, to determine a spatial relationship between the fiducial marker 124 and a coordinate system P of the light source 104, and calibration data representing such calibration may be stored in a calibration data storage block 150 in the storage memory 140 (shown in FIG. 4). In one embodiment, a 1280×960-pixel Flea™ 2 camera (available from Point Grey Research, Inc. of Richmond, British Columbia, Canada) may be used for such calibration to identify a transformation $^{K}T_{P}$ from the coordinate system P of the light source 104 to a coordinate system K of the fiducial marker 124. In one embodiment, twelve images from the Flea™ 2 camera with 98 points each were used for such a calibration, and the calibration used Bouguet's Camera Calibration Toolbox as described in Bouguet, J.-Y., Visual Methods for Three-dimensional Modeling, PhD Thesis (1999), which is based on Zhang's algorithm as described in Zhang, Z. A., Flexible New Technique for Camera Calibration, IEEE T PAMI, 22, 1330-1334 (2000), by modelling the light source 104 as a camera in reverse. In the embodiment shown, the camera 102 is calibrated according to a coordinate system C in the field of view 110 of the camera 102, and such calibration data may also be stored in the calibration data storage block 150.

In the embodiment shown in FIG. 1, the fiducial marker 124 is in the field of view 110 of the camera 102, and referring to FIG. 4, program codes 152 in the program memory 142 include blocks of code that direct the microprocessor 136 to generate a three-dimensional surface map of points on the surface 134 using image data of the fiducial marker 124 received in the field of view 110 of the camera 102.

Figure 5:
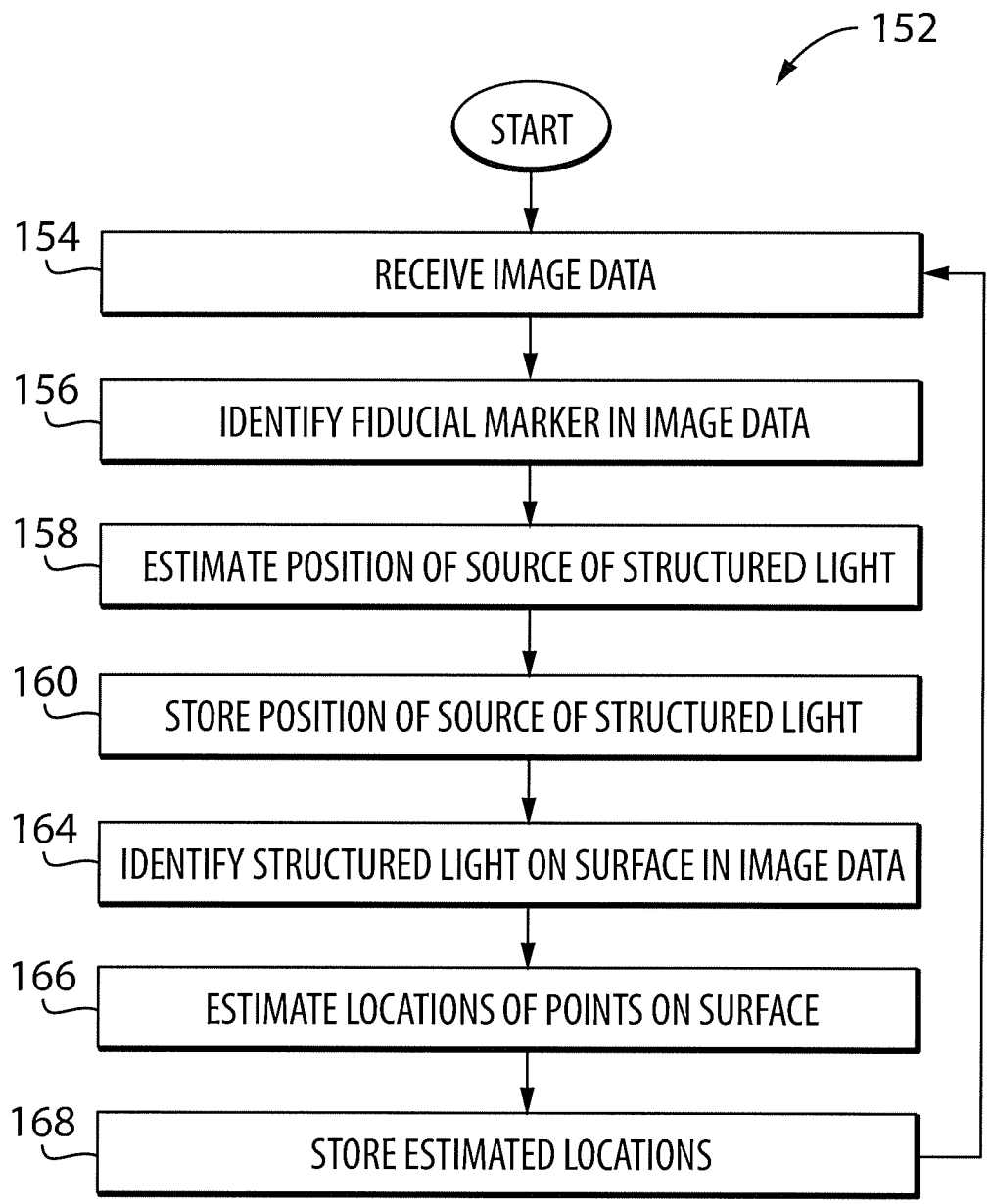
FIGS. 5-8 are schematic illustrations of program codes in a program memory of the computer of FIG. 4.

Referring to FIGS. 4 and 5, the program codes 152 begin at block 154, which includes codes for directing the microprocessor 136 to receive image data of one image frame of video image data from the field of view 110 of the camera 102. As indicated above, the camera 102 is a stereoscopic camera, but the image data received at block 154 is not necessarily stereoscopic image data. Rather, the program codes 152 may generate a three-dimensional surface map of points on the surface 134 from monoscopic image data, and in alternative embodiments the camera 102 may be a monoscopic camera. However, in the embodiment shown, the camera 102 is a stereoscopic camera, but the image data received at block 154 are not necessarily stereoscopic image data. The program codes 152 then continue at block 156, which includes codes for directing the microprocessor 136 to identify the fiducial marker 124 on the light source 104 and in the image data received at block 154. The fiducial marker 124 as shown in FIG. 1 includes only one two-dimensional label, but in some embodiments the fiducial marker may include more than one label, and in such embodiments the codes at block 156 may direct the microprocessor 136 to identify more than one such label in the image data received at block 154. In some embodiments, the inner 2×6 checks and associated saddle may be used for tracking.

The program codes 152 then continue at block 158, which includes codes for directing the microprocessor 136 to estimate a position of the light source 104, which is the source of the structured light 132. The estimated position of the light source 104 may include an estimated linear position and an estimated angular position, overall including three translation values and three rotation values. When, at block 156, the fiducial marker 124 is identified in the image data received at block 154, the position of the fiducial marker 124 in the field of view 110 of the camera 102 may be represented as a transformation $^{C}T_{K}$ from the coordinate system K of the fiducial marker 124 to the coordinate system C of the camera 102. As indicated above, the calibration data storage block 150 stores a transformation $^{K}T_{P}$ from the coordinate systems P of the light source 104 to the coordinate system K of the fiducial marker 124, and the transformation $^{C}T_{P} = {}^{C}T_{K} \times {}^{K}T_{P}$ represents a position of the light source 104 relative to the camera 102. The codes at block 158 therefore direct the microprocessor 136 to determine an estimated position of the light source 104 according to representations of the fiducial marker 124 in the image data received at block 154.

The program codes 152 then continue at block 160, which includes codes for directing the microprocessor 136 to store the transformation $^{C}T_{P}$ in a storage block 162 for the position of the source of structured light in the storage memory 140.

The program codes 152 then continue at block 164, which includes codes for directing the microprocessor 136 to identify the structured light 132 on the surface 134 (shown in FIG. 1) in the image data received at block 154. The program codes 152 then continue at block 166, which includes codes for directing the microprocessor 136 to estimate three-dimensional locations of points on the surface 134 that are indicated by the structured light 132 on the surface 134 (shown in FIG. 1).

In one embodiment, saddle points or distortions of the structured light 132 on the surface 134 may be identified, or the structured light 132 on the surface 134 may otherwise be reconstructed, according to a method similar to the methods described in Geng, J., Structured-Light 3D Surface Imaging: a Tutorial, Advances in Optics and Photonics, 3, 128-160 (2011), according to a method similar to the methods described in Bouguet, J.-Y., Visual Methods for Three-dimensional Modeling, PhD Thesis (1999), or according to a method similar to the methods described in J. Salvi, J. Pagés, J. Batlle, Pattern Codification Strategies in Structured Light Systems, Pattern Recognition 37(4), pp. 827-849, April 2004, for example. Alternatively, automatic tracking algorithms as discussed in Pratt, P., Di Marco, A., Payne, C., Darzi, A., Yang, G.-Z., Intraoperative ultrasound guidance for transanal endoscopic microsurgery, in Ayache, N., Delingette, H., Golland, P., Mori, K. (eds.), MICCAI 2012, Part I, LNCS, vol. 7510, pp. 463-470, Springer, Heidelberg (2012) and in Hughes-Hallett, A., Pratt, P., Mayer, E., Di Marco, A., Yang, G.-Z., Vale, J Darzi, Intraoperative Ultrasound Overlay in Robot-assisted Partial Nephrectomy: First Clinical Experience, Eur Urol. 65(3), 671-2 (2014) may be used.

In the embodiment shown, the codes at block 166 include codes for directing the microprocessor 136 to detect saddle points of the structured light 132 on the surface 134, and such saddle points are at the points of shortest distance between corresponding rays V and R of the light source 104 and the camera 102 respectively. In some embodiments, the codes at block 166 include codes for directing the microprocessor 136 to use the position of the light source 104 relative to the camera 102 as described above with reference to block 158 and epipolar constraints to help identify points or features (such as saddle points, for example) of the structured light 132 on the surface 134 by calculating the correspondence between such points or other features in the structured light 132 and the same points or other features as identified in the image data received from the field of view 110 of the camera 102.

The codes at block 166 direct the microprocessor 136 to identify locations of such saddle points of the structured light 132 on the surface 134 by solving scalar parameters s and u according to $$^{C}[sR_x, sR_y, sR_z, s]' = {}^{C}T_{P} \times {}^{P}[uV_x, uV_y, uV_z, u]'$$

and according to the Caltech Camera Calibration stereo triangulation toolbox described in Bouguet, J.-Y., Visual Methods for Three-dimensional Modeling, PhD Thesis (1999). The codes at block 166 therefore direct the microprocessor 136 to determine estimated locations, in a three-dimensional co-ordinate system, of points on the surface 134 exposed to the structured light 132 according to the image data received at block 154 and according to the estimated position of the source of structured light as determined at block 158.

The program codes 152 then continue at block 168, which includes codes for directing the microprocessor 136 to store the estimated locations of the saddle points of the structured light 132 on the surface 134 (or more generally of other points of the structured light 132 on the surface 134), which are estimated locations of the surface 134, in a surface map of points storage block 170 in the storage memory 140. The surface map of points in the surface map of points storage block 170 may be displayed on the display screen 108, for example to assist a surgeon to control surgical tools on or around the surface 134. Because the light source 104 is independently movable relative to the camera 102, the imagery system 100 can benefit from wide-base triangulation relative to a relatively narrow-base triangulation from a stereoscopic camera, and such wide-base triangulation may be more accurate than such narrow-base triangulation from a stereoscopic camera, for example.

Blocks 154, 156, 158, 160, 164, 166, and 168 as described above may be repeated for each image frame of video image data received from the camera 102, or in some embodiments at least ten times per second. Each time blocks 154, 156, 158, 160, 164, 166, and 168 are repeated, the codes at block 158 may identify a different $^{C}T_{K}$ and recalculate the surface map of points in the surface map of points storage block 170 because the camera 102 and the light source 104 can move relative to each other. Further, each time blocks 154, 156, 158, 160, 164, 166, and 168 are repeated, surface on the display screen 108 may be updated, and embodiments in which blocks 154, 156, 158, 160, 164, 166, and 168 are repeated at least ten times per second may simulate real-time dynamic imaging of the surface 134.

In alternative embodiments, the camera 102 may function as a stereoscopic camera, and in such embodiments, the image data received from the field of view 110 of the camera 102 does not necessarily have to include the fiducial marker 124 or any of the light source 104. For such embodiments, program codes 172 in the program memory 142 (shown in FIG. 4) include blocks of code that direct the microprocessor 136 to generate a surface map of points on the surface 134 using stereoscopic image data.

Figure 6:
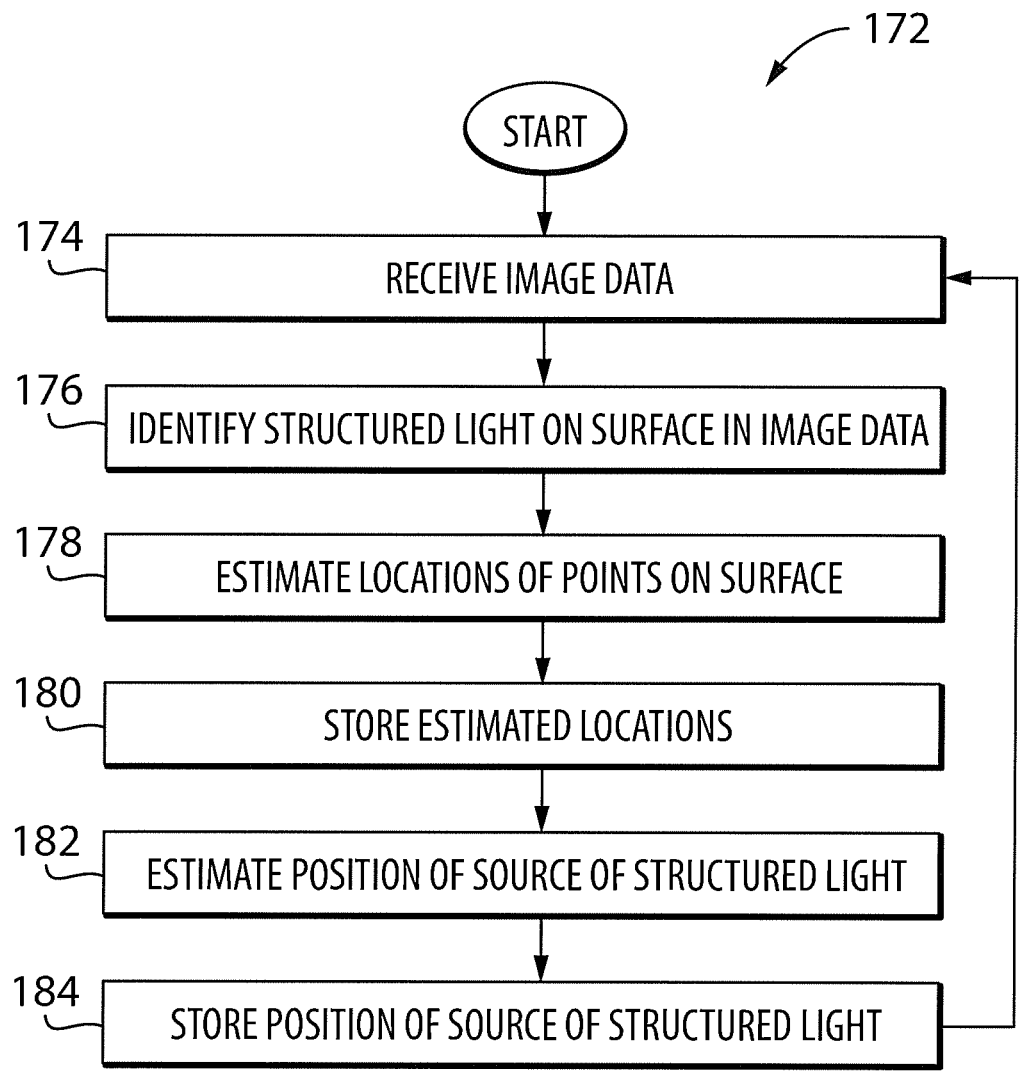

Referring to FIGS. 4 and 6, the program codes 172 begin at block 174, which includes codes for directing the microprocessor 136 to receive stereoscopic image data of one image frame of video image data from the field of view 110 of the camera 102. The program codes 172 then continue at block 176, which includes codes for directing the microprocessor 136 to identify, in the image data received at block 174, the structured light 132 on the surface 134.

The program codes 172 then continue at block 178, which includes codes for directing the microprocessor 136 to do stereo matching and identify points (such as saddle points or other points) of the structured light 132 on the surface 134 using the stereoscopic image data received at block 174. Such stereoscopic image data may be interpreted by triangulation of images received through both the lenses 112 and 114 to identify locations of the points in the three-dimensional coordinate system C of the camera 102, for example using a semi-global block matching approach to determine correspondence or according to a method as described in Ma, Shiwei, Yujie Shen, Junfen Qian, Hui Chen, Zhonghua Hao, and Lei Yang, "Binocular structured light stereo matching approach for dense facial disparity map" in AI 2011: Advances in Artificial Intelligence, pp. 550-559, Springer Berlin Heidelberg, 2011, or as described in Hirschmüller, Heiko, "Stereo processing by semiglobal matching and mutual information" Pattern Analysis and Machine Intelligence, IEEE Transactions on 30, no. 2 (2008): 328-341, as described in Bouguet, J.-Y., Visual Methods for Three-dimensional Modeling, PhD Thesis (1999), or as described in J. Salvi, J. Pagés, J. Batlle, Pattern Codification Strategies in Structured Light Systems, Pattern Recognition 37(4), pp. 827-849, April 2004, for example. Alternatively, automatic tracking algorithms as discussed in Pratt, P., Di Marco, A., Payne, C., Darzi, A., Yang, G.-Z., Intraoperative ultrasound guidance for transanal endoscopic microsurgery, in Ayache, N., Delingette, H., Golland, P., Mori, K. (eds.), MICCAI 2012, Part I, LNCS, vol. 7510, pp. 463-470, Springer, Heidelberg (2012) and in Hughes-Hallett, A., Pratt, P., Mayer, E., Di Marco, A., Yang, G.-Z., Vale, J., Darzi, Intraoperative Ultrasound Overlay in Robot-assisted Partial Nephrectomy: First Clinical Experience, Eur Urol. 65(3), 671 -2 (2014) may be used. The codes at block 166 therefore direct the microprocessor 136 to determine estimated locations, in a three-dimensional co-ordinate system, of points on the surface 134 exposed to the structured light 132 according to the image data received at block 174.

The program codes 172 then continue at block 180, which includes codes for directing the microprocessor to store the estimated locations in the surface map of points storage block 170. The surface map of points in the surface map of points storage block 170 may be displayed on the display screen 108, for example to assist a surgeon to control surgical tools on or around the surface 134.

The program codes 172 then continue at block 182, which includes codes for directing the microprocessor 136 to estimate a position of the light source 104. The position of the projector may be estimated by back projecting the structured light pattern on the surface 134 to determine the projector position that would most accurately recreate the structured light pattern. The codes at block 182 therefore direct the microprocessor 136 to determine an estimated position of the light source 104 according to the image data received at block 174. The program codes 172 then continue at block 184, which includes codes for directing the microprocessor 136 to store $^{C}T_P$ in the storage block 162.

Blocks 174, 176, 178, 180, and 182 as described above may be repeated for each image frame of video image data received from the camera 102, or in some embodiments at least ten times per second. Each time blocks 174, 176, 178, 180, and 182 are repeated, the codes at block 182 may identify a different $^{C}T_p$ and recalculate the surface map of points in the surface map of points storage block 170 because the camera 102 and the light source 104 can move relative to each other. Further, each time blocks 174, 176, 178, 180, and 182 are repeated, surface on the display screen 108 may be updated, and embodiments in which blocks 174, 176, 178, 180, and 182 are repeated at least ten times per second may simulate real-time dynamic imaging of the surface 134.

As indicated above, the embodiment of FIG. 5 can use monoscopic image data, either from a monoscopic camera or from a stereoscopic camera, whereas the embodiment of FIG. 6 uses stereoscopic image data. Nevertheless, both embodiments involve searching for stereo correspondence of pixels in the two images: In the embodiment of FIG. 6, the search for stereo correspondence involves searching for stereo correspondence by triangulation of images received through both the lenses 112 and 114; and in the embodiment of FIG. 5, the search for stereo correspondence first involves identifying a position of the light source 104 relative to the camera 102 as described above with reference to block 158, and then searching for stereo correspondence between the image data from the field of view 110 of the camera 102 and the light source 104 modeled as a camera in reverse.

Figure 7:
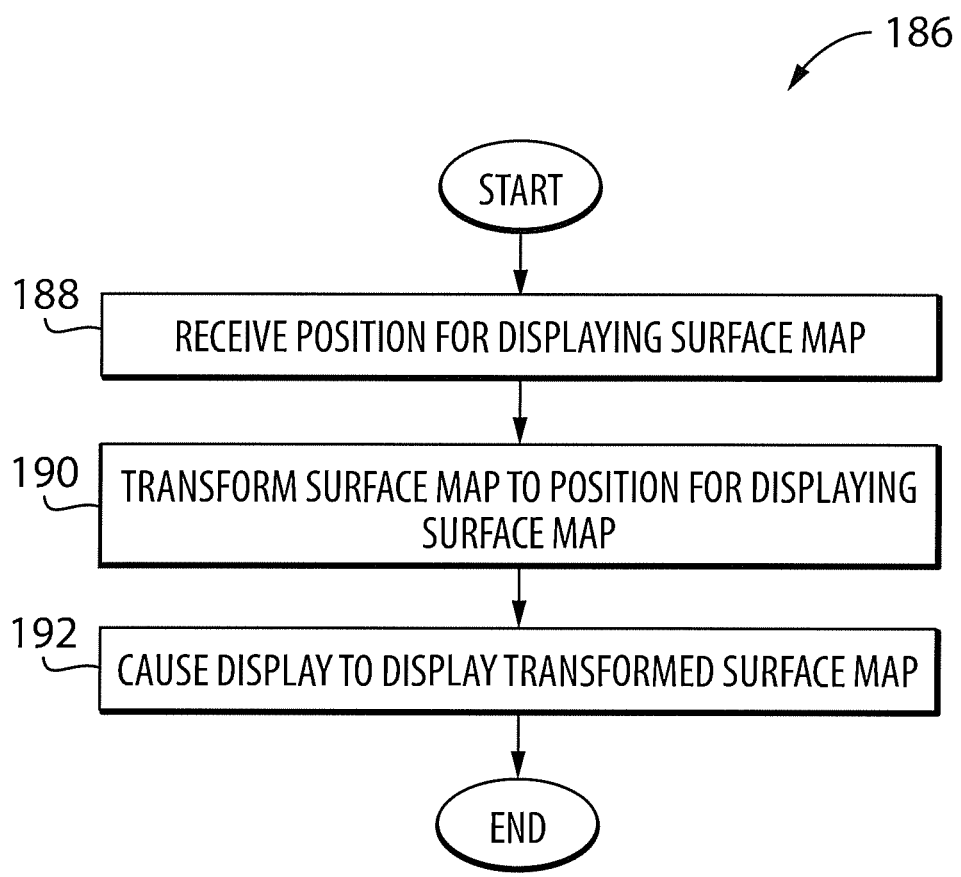

Referring back to FIG. 4, the program memory 142 also includes program codes 186 including blocks of code that direct the microprocessor 136 to cause the display screen 108 to display the surface map of points stored in the surface map of points storage block 170, either at block 168 (shown in FIG. 5) or at block 180 (shown in FIG. 6) as described above. Referring to FIGS. 4 and 7, the program codes 186 begin at block 188, which includes codes for directing the microprocessor 136 to receive, from a user of the computer 106, a position for displaying the surface map of points. The position may be a point of view of the camera 102, or a different position that may be convenient for the user of the computer 106. The program codes 186 then continue at block 190, which includes codes for directing the microprocessor 136 to transform the surface map of points as stored in the surface map of points storage block 170 to the position received at block 188. The program codes 186 then continue at block 192, which includes codes for directing the microprocessor 136 to cause the display screen 108 to display the surface map of points as transformed at block 190. The program codes 186 then end.

Referring back to FIG. 4, the storage memory 140 includes a surgical guidance information storage block 194, which may store surgical guidance information such as information indicating positions of anatomical features such as blood vessels or cancerous tumors on or below the surface 134, and such surgical guidance information may be stored in the surgical guidance information storage block 194 in the coordinate system C of the camera 102. The program memory 142 also includes surgical guidance information program codes 196, which include blocks of codes that direct the microprocessor 136 to cause the light source 104 to display surgical guidance information from the surgical guidance information storage block 194 on the surface 134.

Figure 8:
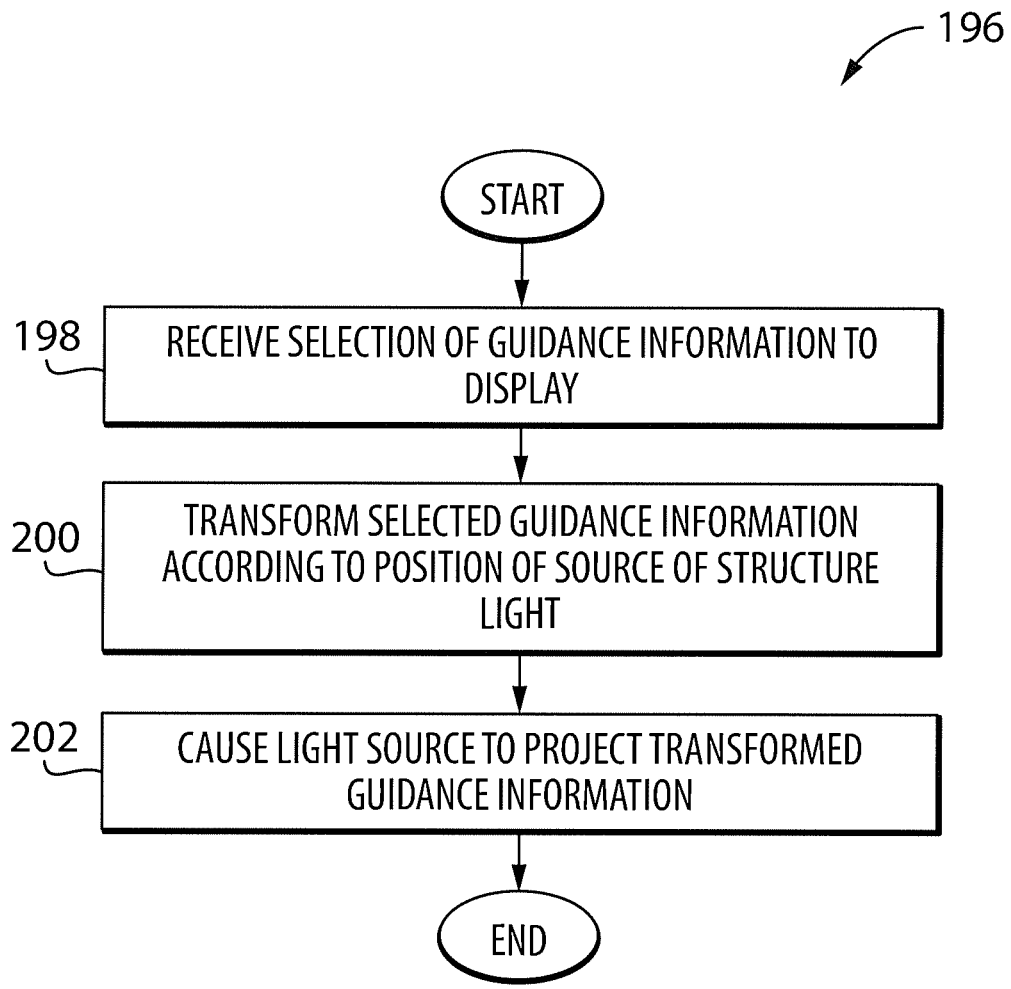

Referring to FIGS. 4 and 8, the program codes 196 begin at block 198, which includes codes for directing the microprocessor 136 to receive, from the user of the computer 106, selection of surgical guidance information from the surgical guidance information storage block 194. The program codes 196 then continue at block 200, which includes codes for directing the microprocessor to transform the selected surgical guidance information to the coordinate system P of the light source 104. For example, if the surgical guidance information is stored in the surgical guidance information storage block 194 in the coordinate system C of the camera 102, then the codes at block 200 direct the microprocessor to transform the coordinates of the surgical guidance information to the coordinate system P of the light source 104 according to the transformation $(^{C}T_P)^{-1}$, which may depend on the estimated position of the light source 104 as determined either at block 158 (shown in FIG. 5) or at block 182 (shown in FIG. 6) and stored in the storage block 162 as described above. The program codes 196 then continue at block 202, which includes codes for directing the microprocessor 136 to cause the light source 104 to project the surgical guidance information selected at block 198 and as transformed at block 200 on the surface 134. The program codes 196 then end.

Figure 9:
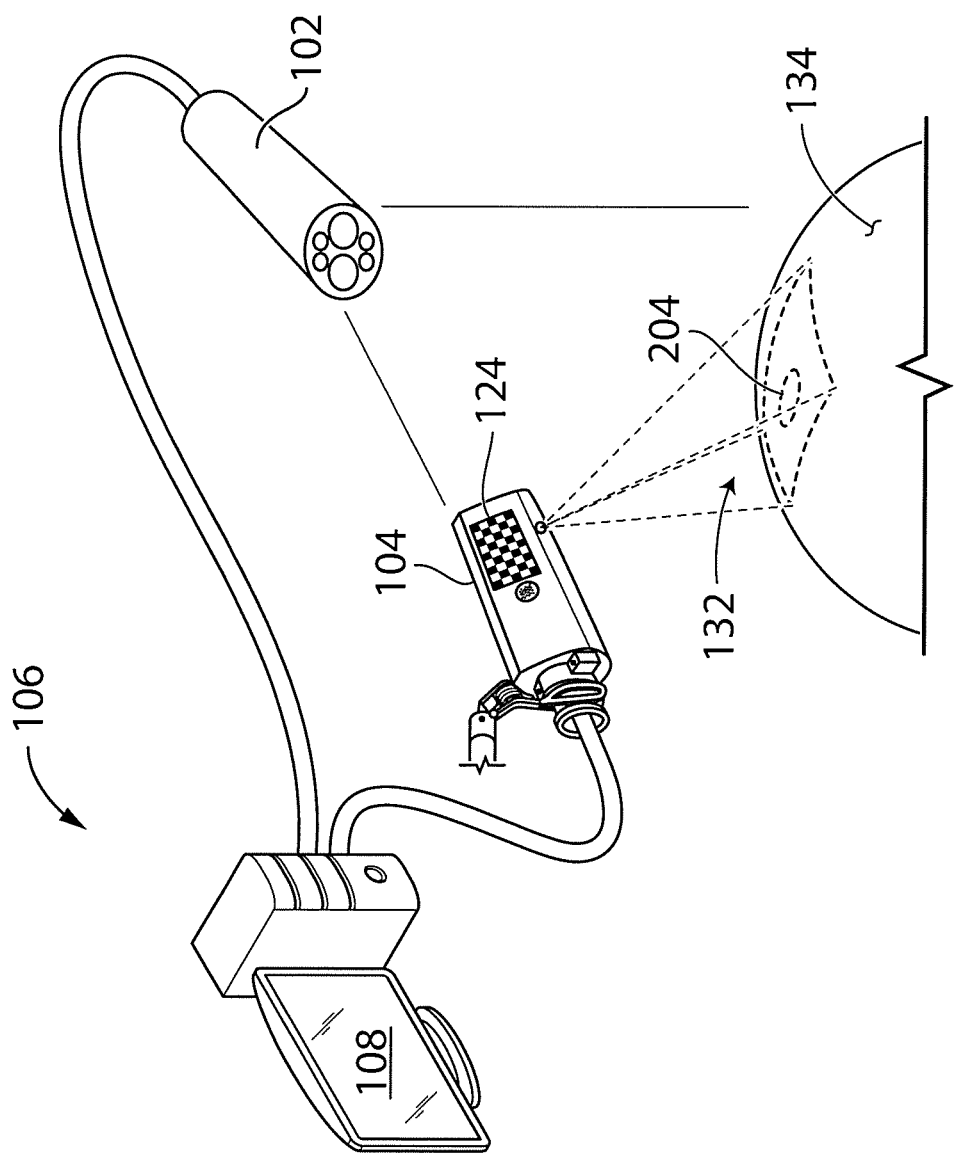
FIG. 9 is a perspective view of the imagery system of FIG. 1, illustrating surgical guidance information projected by the light source of FIG. 2.

Referring to FIG. 9, surgical guidance information 204 is shown on the surface 134. In some embodiments, the surgical guidance information may indicate anatomical features such as blood vessels or cancerous tumors, or may indicate different tissues or different surfaces with different colors. When the light source 104 projects the surgical guidance information 204 on the surface 134, the structured light 132 may be projected as light having one or more frequencies that are invisible to human eyes but visible to the camera 102 so that the surgical guidance information 204 or other images in the field of view 110 of the camera 102 are not obscured by the structured light 132, and FIG. 9 illustrates an embodiment in which the structured light 132 is invisible to a human eye but visible to the camera 102. However, in other embodiments, the structured light 132 may be projected as light having one or more frequencies that are visible to human eyes but filtered to remove the one or more frequencies of the structured light so that the structured light 132 does not obscure the surgical guidance information 204 or other images in the field of view 110 of the camera 102. When the surgical guidance information 204 is in the field of view 110 of the camera 102, image data received from the field of view 110 of the camera 102 may include the surgical guidance information 204 so that the display screen 108 can include the surgical guidance information 204, for example to assist a surgeon to control surgical tools on or around the surface 134. The guidance information 204 may also be updated at least ten times per second, which may simulate real-time dynamic augmented reality.

FIG. 9 illustrates an embodiment in which the light source 104 projects surgical guidance information 204 on the surface 134, but in other embodiments, surgical guidance information may additionally or alternatively be displayed on the display 108. In such embodiments, the display 108 may superimpose the surgical guidance information transformed to the same position (such as the position received at block 188, for example) as the position from which other images are displayed on the display 108.

Over time, the surface map of points stored in the surface map of points storage block 170 may vary, for example as blood vessels under the surface 134 pulsate. The program memory 142 includes surface movements program codes 206 including blocks of code that direct the microprocessor 136 to detect movement of the surface 134 by detecting changes over time (caused by pulsatile or other periodic motion, for example) in the surface map of points stored in the surface map of points storage block 170.

Figure 10:
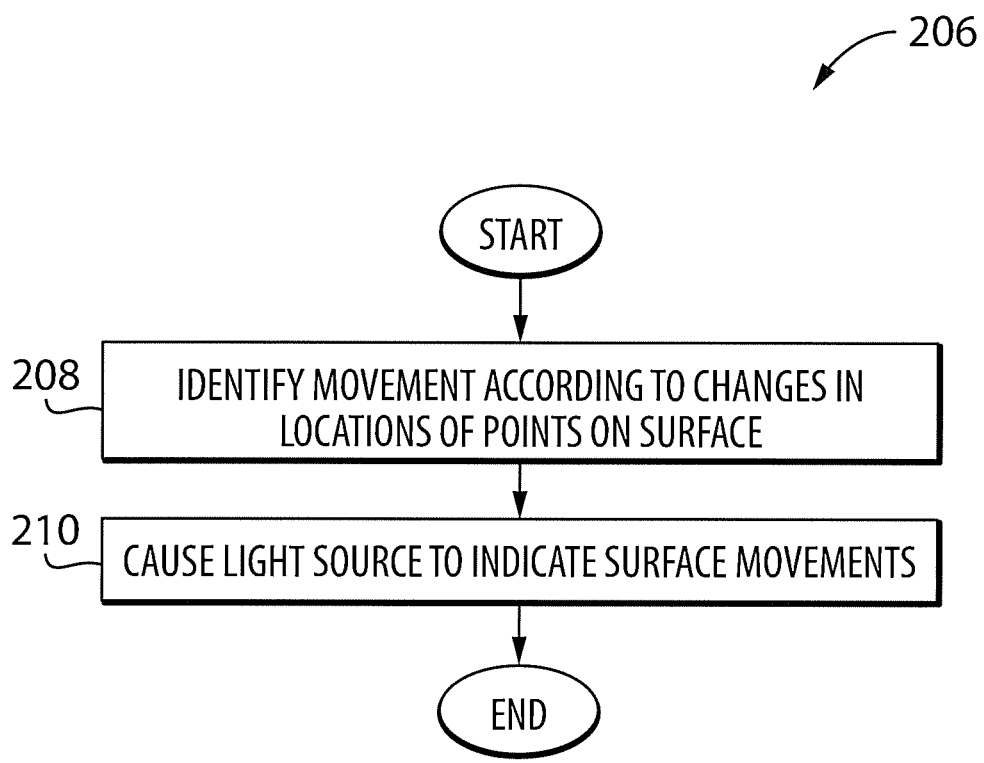
FIG. 10 is a schematic illustration of program codes in the program memory of the computer of FIG. 4.

Referring to FIGS. 4 and 10, the program codes 206 begin at block 208, which includes codes for directing the microprocessor 136 to identify movements according to changes in the locations of points on the surface 134 stored in the surface map of points storage block 170. The program codes 206 then continue at block 210, which includes codes for directing the microprocessor 136 to cause the light source 104 to indicate the surface movements. The program codes 206 then end.

Figure 11:
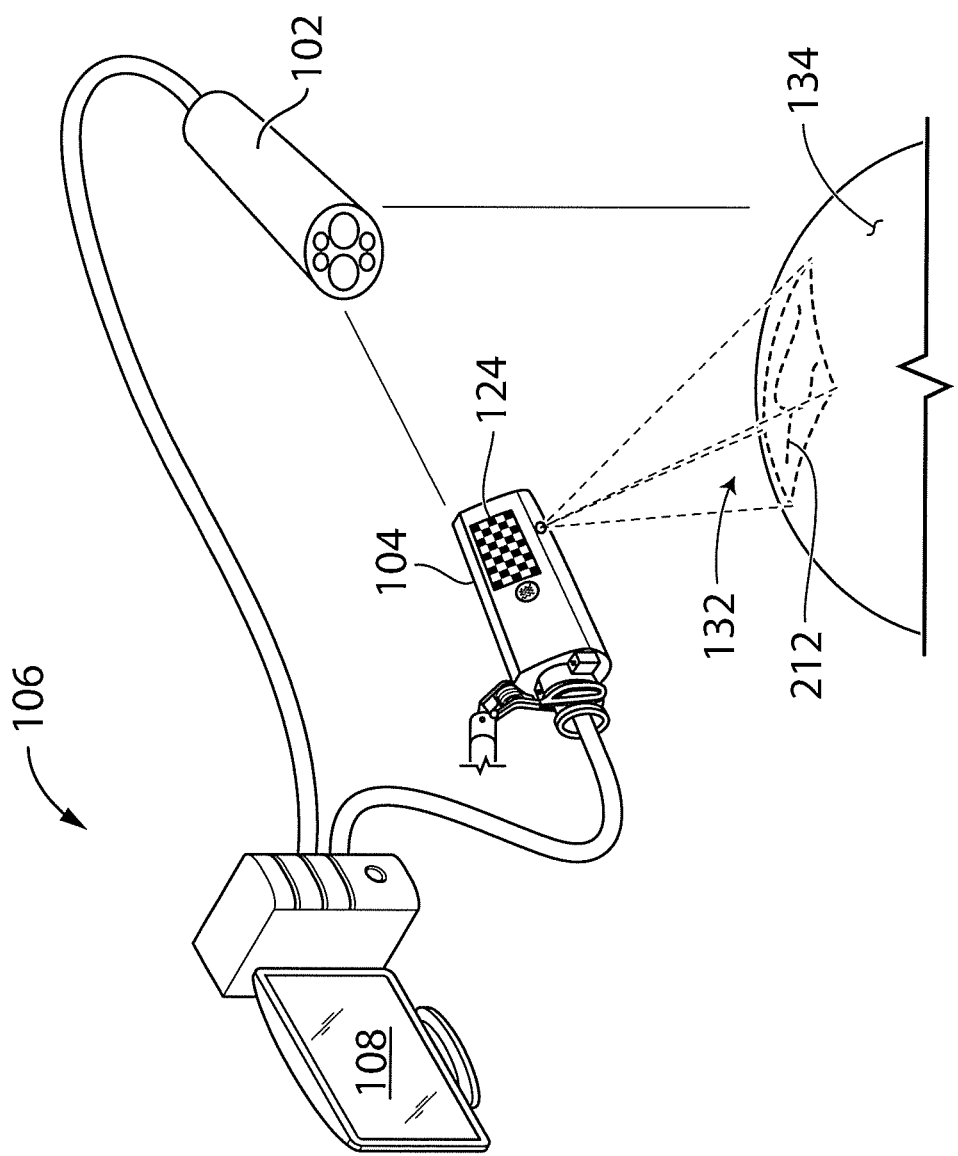
FIG. 11 is a perspective view of the imagery system of FIG. 1, illustrating indications of surface movement projected by the light source of FIG. 2.

As shown in FIG. 11, indications of surface movement 212 may be projected on the surface 134 to indicate regions of the surface 134 that pulsate or otherwise move over time. Again, in the embodiment shown in FIG. 11, the structured light 132 is invisible to a human eye but visible to the camera 102 so that the structured light 132 does not obscure the indications of surface movement 212 or other images in the field of view 110 of the camera 102. However, in other embodiments, the structured light 132 may be projected as light having one or more frequencies that are visible to human eyes but filtered to remove the one or more frequencies of the structured light so that the structured light 132 does not obscure the indications of surface movement 212 or other images in the field of view 110 of the camera 102. The indications of surface movement 212 may be colored in one or more different colors, and when the indications of surface movement 212 are in the field of view 110 of the camera 102, image data received from the field of view 110 of the camera 102 may include the indications of surface movement 212 so that the display screen 108 can include the indications of surface movement 212, which may assist a surgeon to identify movement (such as pulsatile motion, for example) in the surface 134, which may assist the surgeon to control surgical tools on or around the surface 134. The indications of surface movement 212 may also be updated at least ten times per second, which may simulate real-time dynamic augmented reality.

In general, the surgical guidance information 204 and the indications of surface movement 212 may be dots, lines, geometric patterns, or arbitrary patterns, and dots or other patterns may have a greater density of points near areas of greater curvature or gradient, and a lesser density of points near areas of lesser curvature or gradient.

Figure 12:
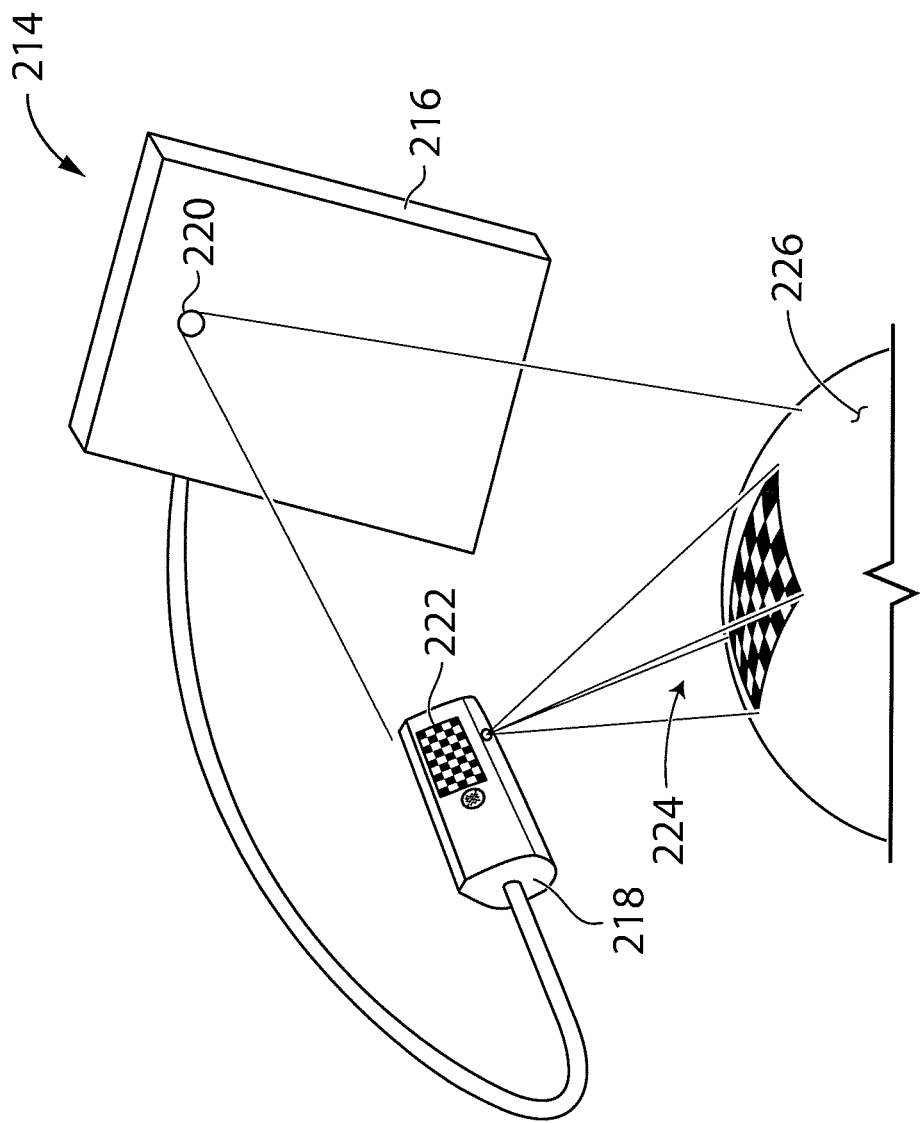
FIG. 12 is a perspective view of an imagery system according to another embodiment.

Referring to FIG. 12, a system according to another embodiment is shown generally at 214 and includes a smartphone 216 and a source of structured light 218. The smartphone 216 includes a smartphone camera 220 that may function as a monoscopic camera as described above with reference to FIGS. 1 and 5. The source of structured light 222 may operate substantially as described above with reference to the light source 104, by projecting structured light shown generally at 224 on to a surface 226. Therefore, embodiments disclosed herein are not limited to surgical applications, but may include other cameras such as a smartphone camera or a tablet-computer camera, for example.

The light source 104 may, in some embodiments, be inserted into a body cavity (through a cannula or through an incision, for example) during minimally invasive surgery and, once in the body cavity, moved using a laparoscopic tool (such as the laparoscopic tool 122, for example) to a position that a surgeon may choose to project structured light onto a surface (such as the surface 134 as described above, for example) in a region of interest in the body cavity to provide imaging of the surface as described above, which may for example be more useful to the surgeon than imaging according to other imaging systems for minimally invasive surgery.

Embodiments such as those described herein may facilitate real-time dynamic surface depth recovery or surface reconstruction in the field of view 110 of the camera 102, and may facilitate augmented reality by projecting information (such as the surgical guidance information 204 or the indications of surface movement 212, for example) in addition to the structured light, which have one or more frequencies that are invisible to the human eye, or that may be filtered, to avoid obscuring the other information. In various embodiments, structured light from light sources as described herein may provide fast and accurate imaging information, even of smooth featureless organ surfaces, and embodiments may be low-cost compared to other imaging systems. Embodiments such as those described herein may also display surface information from viewpoints other than a viewpoint of a camera, which may improve a person's spatial perception.

Therefore, embodiments such as those described herein may include surgical tools or other imaging systems that may provide useful information about a surface (such as the surface 134 or the surface 226 as described above, for example) during minimally invasive surgery such as laparoscopic surgery, or in other applications. The light source 104 could also be used for other purposes, for example as a supplementary light source that can cast shadows of small surface features when lit from a shallow angle.

Although specific embodiments have been described and illustrated, such embodiments should be considered illustrative only and not as limiting the invention as construed according to the accompanying claims.

The invention claimed is:

1. An imagery system comprising:
   a camera having a field of view;
   a light source comprising a source of structured light and at least one fiducial marker on a surface of the light source and visible externally from the light source, the light source movable relative to the field of view of the camera; and
   at least one processor programmed to determine, at least:
      an estimated position of the source of structured light according to representations of the at least one fiducial marker on the surface of the light source in image data received from the field of view of the camera when the at least one fiducial marker on the surface of the light source is in the field of view of the camera; and
      estimated locations, in a three-dimensional co-ordinate system, of points on a surface exposed to the structured light according to representations in the image data of the structured light on the surface exposed to the structured light, and according to the estimated position of the source of structured light.

2. The system of claim 1 wherein the at least one fiducial marker comprises at least one two-dimensional label on the light source.

3. The system of claim 1 wherein the at least one processor is further programmed to cause the light source to project surgical guidance information on human or animal tissue according to the estimated position of the source of structured light.

4. The system of claim 1 wherein the at least one processor is further programmed to:
   identify at least one location, on the surface exposed to the structured light, having surface movements; and
   cause the light source to project light indicating the surface movements on the at least one location, on the surface exposed to the structured light, having the surface movements.

5. The system of claim 1 wherein the light source comprises a tool interface configured to be held by a laparoscopic tool in a unique stable position relative to the laparoscopic tool.

6. The system of claim 1 wherein the at least one processor is further programmed to:
   generate a representation of the points, on the surface exposed to the structured light, from a point of view different from a point of view of the camera.

7. The system of claim 1 wherein the light source is independently movable relative to the field of view of the camera.

8. The system in claim 1 wherein the light source is sized to fit through a cannula of a laparoscopic trocar.

9. The system of claim 1 wherein the light source is sized to fit through an orifice having a diameter less than 15 millimeters.

10. The system of claim 1 wherein the estimated position of the source of structured light comprises an estimated linear position and an estimated angular position of the source of structured light.

11. The system of claim 1 wherein the camera is a laparoscopic camera.

12. The system of claim 1 wherein the camera is a smartphone camera.

13. The system of claim 1 wherein the at least one processor is programmed to determine the estimated locations of the points, on the surface exposed to the structured light, at a rate of at least ten times per second.

14. The system of claim 1 wherein the light source is a source of multi-color light.

15. The system of claim 1 wherein the light source is sterilizable.

16. The system of claim 1 wherein the light source comprises one or more laser diodes and a mirror movable relative to the one or more laser diodes and positioned to direct light from the one or more laser diodes.

17. The system of claim 1 wherein:
   the light source comprises a housing comprising the surface of the light source; and
   the at least one fiducial marker is on the housing.

18. The system of claim 1 wherein the at least one fiducial marker comprises a fiducial marker selected from the group consisting of a checkerboard pattern on a two-dimensional label on the light source, a matrix barcode on the light source, an asymmetric dot pattern on the light source, a plurality of light-emitting diodes on the light source, a plurality of reflective markers on the light source, and one or more markers on the light source for an electromagnetic tracker.

19. The system of claim 7 wherein the light source is independently movable in six degrees of freedom relative to the field of view of the camera.

20. The system of claim 1 wherein the at least one processor is programmed to determine the estimated locations of the points on the surface exposed to the structured light according to a transformation from a coordinate system of the structured light to a coordinate system of the at least one fiducial marker and according to a transformation from the coordinate system of the at least one fiducial marker to a coordinate system of the camera.

21. The system of claim 1 wherein the light source is movable within the field of view of the camera.

22. A method of guiding surgery on human or animal tissue, the method comprising:
   causing a light source of an imagery system to project surgical guidance information on the human or animal tissue, wherein the imagery system comprises:
   a camera having a field of view;
   the light source comprising a source of structured light and at least one fiducial marker on a surface of the light source and visible externally from the light source, the light source movable relative to the field of view of the camera; and
   at least one processor programmed to, at least:
      determine an estimated position of the source of structured light according to representations of the at least one fiducial marker on the surface of the light source in image data received from the field of view of the camera when the at least one fiducial marker on the surface of the light source is in the field of view of the camera;

determine estimated locations, in a three-dimensional co-ordinate system, of points on a surface exposed to the structured light according to representations in the image data of the structured light on the surface exposed to the structured light, and according to the estimated position of the source of structured light; and cause the light source to project the surgical guidance information according to the estimated position of the source of structured light.

* * * * *